US00PP16200P3

(12) United States Plant Patent
Coiner

(10) Patent No.: US PP16,200 P3
(45) Date of Patent: Jan. 10, 2006

(54) HYBRID TEA ROSE PLANT NAMED 'TANTALIZING RED'

(50) Latin Name: *Rosa hybrida*
Varietal Denomination: Tantalizing Red

(75) Inventor: James W. Coiner, La Verne, CA (US)

(73) Assignee: Coiner Nursery, LaVerne, CA (US)

( * ) Notice: Subject to any disclaimer, the term of this patent is extended or adjusted under 35 U.S.C. 154(b) by 110 days.

(21) Appl. No.: 10/016,070

(22) Filed: Dec. 5, 2001

(65) Prior Publication Data

US 2003/0106116 P1 Jun. 5, 2003

(51) Int. Cl.
*A01H 5/00* (2006.01)

(52) U.S. Cl. ..... Plt./130

(58) Field of Classification Search ..... Plt./130, Plt./139, 140
See application file for complete search history.

*Primary Examiner*—Howard J. Locker
(74) *Attorney, Agent, or Firm*—Christie, Parker & Hale, LLP

(57) ABSTRACT

A new and distinct Hybrid Tea Rose plant variety with red-purple flowers.

1 Drawing Sheet

Classification: The present invention relates to a new *Rosa hybrida* plant.

Variety denomination: The new plant has the varietal denomination 'Tantalizing Red'.

BACKGROUND OF THE INVENTION

The present invention relates to a new and distinct variety of rose plant of the hybrid tea rose of the genus *Rosaceae* which was created by crossing as seed and pollen parents two (2) unknown rose varieties. The varietal denomination of the new variety is 'Tantalizing Red'.

SUMMARY OF THE INVENTION

Among the novel characteristics possessed by this new variety which distinguishes it from other varieties of which I am aware, is its attractive red-purple flowers.

Asexual reproduction by budding of the new variety onto 'Dr. Huey' rootstock as performed in Wasco, Calif. shows that the foregoing and other distinguishing characteristics come true to form and are established and transmitted through succeeding propagations.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE NEW VARIETY

The following is a detailed description of 2-year budded plants of the new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of specimens grown outdoors in Wasco, Calif., during November and budded on understock of 'Dr. Huey'.

Plant:

*Form.*—Upright.

*Growth.*—Vigorous, non-uniform.

*Size.*—Height about 6 feet; width about 3 feet.

*Disease resistance.*—Cultivar exhibits average resistance/susceptibility to disease.

*Foliage.*—Size: Terminal leaflet length about 2½ inches, width about 1¾ inches; leaf about 5½ inches long and about 4 inches wide. Quantity: Compound leaf with 3, 5, or 7 leaflets. Color: New foliage: Upper side near 146A; under side near 182B. Mature foliage: Upper side near 147A; under side near 147C. Shape: Elliptic. Texture: Upper side: Smooth, semi-glossy. Under side: Matte. Edge: Serrated. Serration: Slight.

*Petioles.*—Top surface color near 144B; Under side near 144A.

*Stipules.*—Normal.

*Auricle.*—Slight serration near 59B to 137C.

*Rachis.*—Smooth.

Wood:

*New shoots.*—Bark: Smooth. Wood: Near 59C.

*Old wood.*—Bark: Smooth. Wood: Near 146B.

*Flowering stem.*—Length about 24 inches.

*Winter hardiness.*—Completely winter hardy.

*Preferred growing conditions.*—Full sun.

*Growth habit.*—Upright.

*Leaves per stem.*—About 7.

*Thorns and prickles.*—Average number of prickles and thorns, new thorns about 3/16 inch, near 142B, mature thorns about ⅜ inch near 144B.

Flower/inflorescence:

*Blooming habit.*—Recurrent.

*Bud.*—Average length about 1 3/16 inch, width 1½ inches. Form: High centered classic rose form. Color: Before sepals divide color near 60A; when sepals first divide color near 60C; when petals begin to unfurl color near 63B.

*Sepals.*—Pointed on ends; regular appearance, usually 5 sepals, 1⅛ inch long and ¼ inch wide, occasional extensions.

*Color.*—Topside near 158B; bottom near 144C.

*Peduncle.*—Smooth. Length: About 1¾ inches. Strength: Firm. Color: Near 139B, with anthocyanin blush near 59C.

*Flower.*—Size: About 5 inches. Borne: Multiple blooms per stem. Form: High centered, opening flat with maturity.

*Petalage.*—About 38. Petaloids in center: Few, about 3 to 5 petaloids, color near 74C.

*Fragrance.*—Slight.

*Lasting quality.*—About 3 weeks on plant; about 6 days after cutting.

*Color.*—During first 2 days: Inner petals at flower center topside near 60B; bottom near 60C; outer petals topside near 60B, bottom near 60C.

*Base of petals* (*point of attachment*).—Near 158B.

*General tonality from a distance.*—Dark Red-Purple near 59C.

*Color change.*—As bloom ages, fades slightly to near 60C; after 3 or more days, about the same.

*General tonality from a distance.*—Dark red even after 3 or more days.

*Petals.*—Length: Approximately 1⅛ in. long. Width: Approximately 2 in. wide. Texture: Soft. Shape: Wider than long. Arrangement: Normal. Appearance: Satiny. Margin: Smooth. Persistance: Strong, as a cut flower and in the garden.

Reproductive organs:

*Arrangement of stamens, filaments and anthers.*—Regularly arranged around styles, about 40 to 50 filaments and anthers, no pollen observed.

*Color.*—Filaments near 162B; Anthers near 158B.

*Styles.*—Thin.

*Stigmas.*—Color near 158D.

*Hips/seed vessels/ovaries.*—Shape: Round. Size: About ½ inch. Color: Near 144A. Seeds: No seeds observed.

I claim:

1. A new and distinct Hybrid Tea Rose plant of the variety substantially as shown and described.

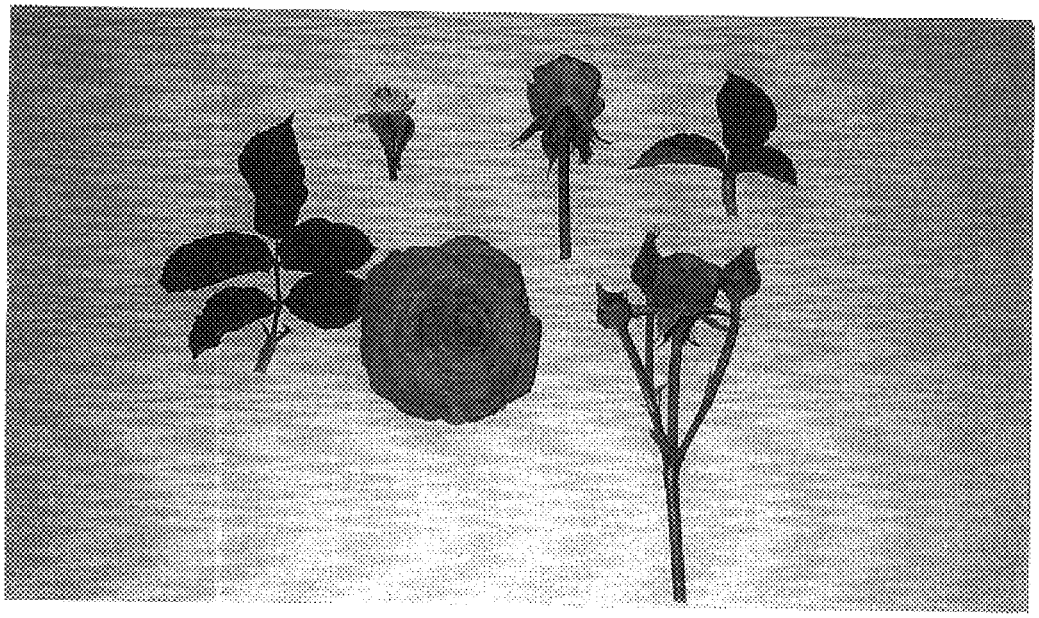

* * * * *